United States Patent [19]

Amann et al.

[11] Patent Number: 4,657,861

[45] Date of Patent: Apr. 14, 1987

[54] S-TETRAHYDROPROTOBERBERINEOXI-DASE, PROCESS FOR PRODUCING THE SAME AND USE THEREOF

[75] Inventors: Manfred Amann, Grunwald, Fed. Rep. of Germany; Naotaka Nagakura, Kobe, Japan; Meinhart H. Zenk, Munich, Fed. Rep. of Germany

[73] Assignee: Consortium fur elektrochemische Industrie GmbH, Munich, Fed. Rep. of Germany

[21] Appl. No.: 700,510

[22] Filed: Feb. 12, 1985

[30] Foreign Application Priority Data

Feb. 24, 1984 [DE]  Fed. Rep. of Germany ....... 3406774

[51] Int. Cl.$^4$ ..................... C12P 17/10; C12N 9/02; C07B 19/02
[52] U.S. Cl. .................................. 435/121; 435/189; 435/280
[58] Field of Search ................ 435/189, 119, 121, 280

[56] References Cited

U.S. PATENT DOCUMENTS 4,302,540 11/1981 Hirata et al. ..................... 435/280

FOREIGN PATENT DOCUMENTS 57-144992 9/1982 Japan .................................. 435/119
59-159790 9/1984 Japan .................................. 435/119

OTHER PUBLICATIONS

Kamentani et al, Tetrahydron, vol. 29, pp. 2031 to 2033 (1973).
Merck Index, 10th edition, p. 165, entry 1165 and 1162, 1983.

Primary Examiner—Lionel M. Shapiro
Attorney, Agent, or Firm—Collard, Roe & Galgano

[57] ABSTRACT

The invention relates to the enzyme S-tetrahydroprotoberberineoxidase, which oxidizes selectively S-tetrahydroprotoberberines and S-1-benzyl-1,2,3,4-tetrahydroisoquinoline in the presence of oxygen, resulting in the corresponding protoberberines and 1-benzyl-3,4-dihydroisoquinolines. The invention also relates to a process of preparing S-tetrahydroprotoberberineoxidase by extraction from certain plant materials. The oxidation products of several compounds find use in the pharmaceutical industries.

19 Claims, No Drawings

S-TETRAHYDROPROTOBERBERINEOXIDASE, PROCESS FOR PRODUCING THE SAME AND USE THEREOF

The present invention relates to a catalytically active protein. More particularly, it relates to a protein whose catalytic action derives from the oxidation, in the presence of oxygen, of compounds selected from the group consisting of S-tetrahydroprotoberberine and S-1-benzyl-1,2,3,4-teterahydroisoquinolines, with formation of the corresponding protoberberines or the corresponding 1-benzyl-3,4-dihydroisoquinolines, respectively, and hydrogen peroxide.

In particular, the present invention relates to S-tetrahydroprotoberberineoxidase. This enzyme is characterized by the following parameters:

Molar weight: 100,000±10%, determined by gel filtration
Isoelectric point: 5.7
Temperature optimum: 40° C.
pH optimum: 8.9
$K_M$ value for R,S-corypalmine at 40° C. and pH 8.9, 1.3 μMoles
Intensity maximum of the fluorescense-emission spectrum 520 nm at an excitation wavelength of 450 nm.
Complete and reversible inhibition in the presence of acetylacetone or morin
Prosthetic group flavin S-tetrahydroprotoberberineoxidase can be obtained by extraction from plant materials which are selected from the families of Papaveraceae, Berberidaceae, Menispermaceae, Annonaceae and Ranunculaceae.

Examples of suitable plant material from the family of the Papaveraceae are the genus of, e.g., Argemone, Papaver, and Eschscholtzia. Specific examples are, e.g., *Argemone platyceras* and *Eschscholtzia californica*.

An example of plant materials from the family Berberidaceae is the genus Berberis. Specific examples are: *Berberis bedniana*, *Berberis stolonifera*, *Berberis aristata* and *Berberis wilsoniae* var. *subcaulialata*. A special example from the family Menispermaceae is *Cissampelus mucronata* and from the family Ranunculaceae, *Thalictrum glaucum*. From the family Annonaceae, an example is *Annona reticulata*.

The plant material used is preferably from cell cultures, but plants themselves or parts of plants may be processed, e.g., roots are useful for obtaining the enzyme.

The extraction of the plant material is performed by the same methods previously used for extracting enzymes from plants. As a general rule, the process is carried out by first destroying the structure of the cells or of the cell cultures, respectively. For that purpose, the plant material is preferably frozen, e.g., at the temperature of liquid nitrogen, comminuted (if desired) and finally dissolved in an aqueous preparation of pH 6–10. Preferably, a buffer solution, e.g., phosphate buffers, adapted to the aforementioned pH range, is used as the aqueous preparation. If necessary, separation of unchanged materials takes place followed by protein precipitation which occurs by the addition of an electrolyte (especially ammonium sulfate). The precipitated proteins are subsequently dissolved in an aqueous buffer solution (pH 6–10) and subjected to a gel filtration. By the gel filtration there occurs, on the one hand, an elimination of salt, while on the other hand, a separation of the protein mixture present, achieved in accordance with molecular size. For further processing, that part of the eluate from the gel filtration is used which contains the proteins of a molecular weight >70,000. The further cleaning steps comprise the subsequent chromatographic separation of the protein mixture with ion-echangers (e.g., diethylaminoethylcellulose) followed by elution with potassium chloride solutions of varying concentration. The selection of the eluate is always made according to controls of enzymatic activity. If desired, other or additional methods of separation may be used, e.g., electrophoresis, and the like.

The above-described processing operations are carried out in aqueous systems, particularly in buffer solutions having a pH of 6–10, especially 7–9, at temperatures from 4° C. to 15° C.

According to the invention, aqueous or frozen-dried preparations are obtained which have an enzymatic activity corresponding to their content of S-tetrahydroprotoberberineoxidase. The invention therefore relates to enzymatically active preparations containing S-tetrahydroprotoberberineoxidase.

Frequently, it is advantageous to apply the enzyme of the invention in an immobilized state. For that purpose, the enzyme is adsorbed physically or chemically on carrier materials in a manner known, per se. Carrier materials are, e.g., alginates, agaroses with functional groups, cellulose, polyacrylic resins (with e.g., oxirane groups) glasses and silicates.

The enzyme according to the invention catalyzes the oxidation of S-tetrahydroprotoberberine or, respectively, S-1-benzyl-1,2,3,4-tetrahydroisoquinoline in the presence of oxygen, whereby the corresponding protoberberines and, respectively, the 1-benzyl-3,4-dihydroisoquinolines are obtained.

The invention therefore further relates to a process for the enzymatic oxidation of compounds of the formula

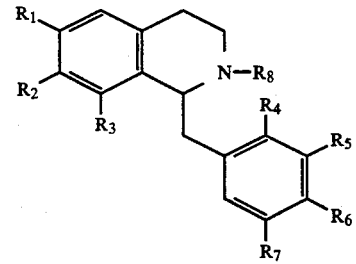

with S-configuration, wherein $R_1$, $R_2$, $R_5$, $R_6$ and $R_7$ are independently selected from the group consisting of, hydrogen atom, hydroxy-, alkyl- and alkoxy groups;
$R_1 + R_2$, as well as, $R_5 + R_6$ may form a dioxaalkylene ring with 1 to 2 methylene groups;
$R_3$ is hydrogen or an —OH group;
$R_4$ stands for hydrogen;
$R_8$ represents hydrogen and an alkyl group with 1–3 carbon atoms, and optionally,
$R_4 + R_8$ may form a methylene bridge and wherein the oxidation occurs in the presence of S-tetrahydroprotoberberineoxidase $R_1$, $R_2$, $R_5$ and $R_6$, preferably, may independently represent hydrogen atom or —OH, methyl, ethyl, methoxy or ethoxy groups. $R_8$ is preferably hydrogen or a methyl group.

Examples of compounds to be oxidized are, e.g., corypalmine, corydalmine, stylopine, isocorypalmine, coramine, stepholidine, discretamine, corytenchirine, capaurimine, reticuline, norreticuline, tetrahydropapaverine, N-methyltetrahydropapaverine, orientaline, isoorientaline, norisoorientaline, nororientaline, protosinomenine, norprotosinomenine, canadine, tetrahydropalmatine, scoulerine, coreximine, coclaurine, N-methylcoclaurine, 1-benzyl-1,2,3,4-tetrahydroisoquinoline
1-benzyl-6-hydroxy-1,2,3,4-tetrahydroisoquinoline
1-benzyl-6-methoxy-1,2,3,4-tetrahydroisoquinoline
1-benzyl-7-hydroxy-1,2,3,4-tetrahydroisoquinoline
1-benzyl-7-methoxy-1,2,3,4-tetrahydroisoquinoline
1-(3'-hydroxy-benzyl)-1,2,3,4-tetrahydroisoquinoline
1-(3'-hydroxy-benzyl)-6-hydroxy-1,2,3,4-tetrahydroisoquinoline
1-(3'-hydroxy-benzyl)-6-methoxy-1,2,3,4-tetrahydroisoquinoline
1-(3'-hydroxy-benzyl)-7-hydroxy-1,2,3,4-tetrahydroisoquinoline
1-(3'-hydroxy-benzyl)-7-methoxy-1,2,3,4-tetrahydroisoquinoline
1-(3',4'-dihydroxy-benzyl)-1,2,3,4-tetrahydroisoquinoline
1-(3',4'-dihydroxy-benzyl)-6-hydroxy-1,2,3,4-tetrahydroisoquinoline
1-(3',4'-dihydroxy-benzyl)-6-methoxy-1,2,3,4-tetrahydroisoquinoline
1-(3',4'-dihydroxy-benzyl-)-7-hydroxy-1,2,3,4-tetrahydroisoquinoline
1-(3',4'-dihydroxy-benzyl)-7-methoxy-1,2,3,4-tetrahydroisoquinoline
1-(3',5'-dihydroxy-benzyl)-6-hydroxy-1,2,3,4-tetrahydroisoquinoline
1-(3',5'-dihydroxy-benzyl)-6-methoxy-1,2,3,4-tetrahydroisoquinoline
1-(3',5'-dihydroxy-benzyl)-7-hydroxy-1,2,3,4-tetrahydroisoquinoline
1-(3',5'-dihydroxy-benzyl)-7-methoxy-1,2,3,4-tetrahydroisoquinoline
1-(3',4'-dimethoxy-benzyl)-1,2,3,4-tetrahydroisoquinoline
1-(3',4'-dimethoxy-benzyl)-6-hydroxy-1,2,3,4-tetrahydroisoquinoline
1-(3',4'-dimethoxy-benzyl)-7-hydroxy-1,2,3,4-tetrahydroisoquinoline
1-(3',4'-dimethoxy-benzyl)-6-methoxy-1,2,3,4-tetrahydroisoquinoline
1-(3',4'-dimethoxy-benzyl)-7-methoxy-1,2,3,4-tetrahydroisoquinoline
1-(3'-methoxy-4'-hydroxy-benzyl)-1,2,3,4-tetrahydroisoquinoline
1-(3'-methoxy-4'-hydroxy-benzyl)-6-hydroxy-1,2,3,4-tetrahydroisoquinoline
1-(3'-methoxy-4'-hydroxy-benzyl)-6-methoxy-1,2,3,4-tetrahydroisoquinoline
1-(3'-methoxy-4'-hydroxy-benzyl)-7-hydroxy-1,2,3,4-tetrahydroisoquinoline
1-(3'-methoxy-4'-hydroxy-benzyl)-7-methoxy-1,2,3,4-tetrahydroisoquinoline
1-(3',5'-dimethoxy-benzyl)-1,2,3,4-tetrahydroisoquinoline
1-(3',5'-dimethoxy-benzyl)-6-hydroxy-1,2,3,4-tetrahydroisoquinoline
1-(3',5'-dimethoxy-benzyl)-7-hydroxy-1,2,3,4-tetrahydroisoquinoline
1-(3',5'-dimethoy-benzyl)-6-methoxy-1,2,3,4-tetrahydroisoquinoline
1-(3',5'-dimethoxy-benzyl)-7-methoxy-1,2,3,4-tetrahydroisoquinoline
1-(3'-hydroxy-4'-methoxy-benzyl)-1,2,3,4-tetrahydroisoquinoline
1-(3'-hydroxy-4'-methoxy-benzyl)-6-hydroxy-1,2,3,4-tetrahydroisoquinoline
1-(3'-hydroxy-4'-methoxy-benzyl)-7-hydroxy-1,2,3,4-tetrahydroisoquinoline
1-(3'-hydroxy-4'-methoxy-benzyl)-6-methoxy-1,2,3,4-tetrahydroisoquinoline
1-(3'-hydroxy-4'-methoxy-benzyl)-7-methoxy-1,2,3,4-tetrahydroisoquinoline
1-(3',4',5'-trihydroxy-benzyl)-1,2,3,4-tetrahydroisoquinoline
1-(3',4',5'-trihydroxy-benzyl)-6-hydroxy-1,2,3,4-tetrahydroisoquinoline
1-(3',4',5'-trimethoxy-benzyl)-6-hydroxy-1,2,3,4-tetrahydroisoquinoline
1-(3',4',5'-trimethoxy-benzyl)-1,2,3,4-tetrahydroisoquinoline
1-(3',4',5'-trimethoxy-benzyl)-6-methoxy-1,2,3,4-tetrahydroisoquinoline The reaction temperatures are 10°–70° C., especially 35°–45° C. The process, according to the invention, is carried out in the presence of oxygen, particularly in the presence of air.

The operation is performed, preferably, by adding to an aqueous preparation of S-tetrahydroprotoberberine or S-1-benzyl-1,2,3,4-tetrahydroisoquinoline, respectively, having a pH of 6–10, especially a pH of 8.9, which may still contain dissolution promoting agents, e.g., dimethylsulfoxide or methanol and the like, a preparation in which the enzyme is present in immobilized form, and stirring in the presence of oxygen, preferably air.

The quantity of enzyme to be added to the substrate, with respect to the amount of the latter, is not critical. It is adjusted in accordance with the desired product conversion. As a rule, per mole of substrate, enzyme amounts of 1–50 g, especially 15–20 g, are added.

The progress of the reaction is, e.g., photometrically controlled. With the above-described process, the S-forms of the tetrahydroprotoberberines or the 1-benzyl-1,2,3,4-tetrahydroisoquinoline, respectively, are selectively oxidized. The process is, therefore, suitable for the separation of the enantiomer mixtures, or for obtaining the R-form from the S-form. The R-forms are not attacked thereby. They may be separated by known methods from the protoberberines or the 1-benzyl-3,4-dihydroisoquinolines, which are obtained by oxidation of the S-forms, e.g., by chromatography.

In a modified form of the described process for the separation of enantiomer mixtures of the tetrahydroprotoberberines or 1-benzyl-1,2,3,4-tetrahydroisoquinolines, respectively, the oxidized species of the S-forms are again reduced under formation of the R-forms or a mixture of R/S, respectively, returning back to the starting compounds. In this manner, an enrichment of the R-form is obtained. As a reducing agent, e.g., sodium boranate may be used.

Preferably, the process for separation of the enantiomers or, respectively, the production of the R-form from the S-form is carried out in a cycle. In that case, it is advantageous to use the enzyme according to the invention in immobilized state. Starting from the enantiomer mixture the cycle comprises the following partial steps:

(a) selective enzymatic oxidation of the S-form while retaining the R-form of the starting products;
(b) reduction of the oxidized products with recovery of the R-form or an R/S mixture, respectively; and
(c) return of the R/S mixture to the oxidation step.

By repeating the cycle several times, the R-forms of the tetrahydroprotoberberine or of the 1-benzyl-1,2,3,4-tetrahydroisoquinoline, respectively, are obtained.

Of technical interest are the R-forms of some tetrahydroprotoberberines, which among other things are used as starting or intermediate products for the preparation of physiologically active alkaloids.

By the process for separation of enantiometer mixtures according to the invention, it is, e.g., possible to convert enantiomer mixtures of reticuline or S-reticuline, respectively, or enantiomer mixtures of norreticuline or S-norreticuline, respectively, into R-reticuline or R-norreticuline, which are valuable intermediates for the synthesis of codeine or morphine.

The invention will now be more fully described in a number of examples, but it should be understood that these are given by way of illustration and not of limitation.

EXAMPLE 1

Preparation of S-tetrahydroprotoberberineoxidase 200 g of a cell culture of Berberis wilsonae var. subcaulialata frozen with liquid nitrogen, were stirred for 20 minutes in 440 ml of an aqueous solution of $KHPO_4/KH_2PO_4$ buffer solution (50 millimolar, pH=7.4). The homogeneous cell preparation so formed was subsequently filtered and centrifuged. To the supernatant layer 236 g ammonium sulfate (to the 70% saturation) were added. The precipitation of protein thus formed was centrifuged and the centrifuged mass dissolved in 20 ml $KHPO_4/KH_2PO_4$-buffer solution (50 millimolar, pH=7.4).

The so-obtained solution was then subjected to a gel filtration on an ultragel AcA 44-column of the firm LKB Bromma, Sweden. The fractions of the eluate which exhibited enzyme activity (tested by the color reaction of S-norreticuline to 1,2-dehydronorreticuline) were collected and admitted to a sepharose separating column (Matrex Blue A, firm Amicon (Wittew, W-Germany). The unfractioned eluate was then adsorbed on DEAE-cellulose (i.e., diethylaminoethyl-cellulose) and extracted with potassium chloride solutions of increasing concentration (from 0 to 300 mmole KCl content).

The enzyme-active fractions were collected, concentrated by ultrafiltration, and freed from salt. The product obtained had a specific activity of 2.2 nkat/mg of protein. The yield was 41.4%.

By discontinuous electrophoresis in polyacrylamide gel, the product was made homogeneous. The gel system used had in the collective gel a pH of 8.3, in the separating gel a pH value of 9.5 with any acrylamide content of 7.5% by weight. The pH value in the electrode buffer was 8.3. The parts of separating gel showing enzymatic activity were finally extracted with 50 millimolar $KHPO_4/KH_2PO_4$-buffer solution.

Specific enzyme activity 6.2 nkat/mg corresponding to a 155-fold enrichment compared to the crude extract. Yield: 25%

EXAMPLE 2

Preparation of immobilized S-tetrahydroprotoberberineoxidase 6 ml of an enzyme preparation of S-tetrahydroprotoberberineoxidase in an aqueous buffer solution of boric acid/sodium borate/HCl (0.1 molar, pH=8.9) with an enzyme activity of 2.2 nkat/mg and a protein content of 1.12 mg/ml, were added in 50 ml of a 5% by weight aqueous alginate solution while stirring. Subsequently, the enzyme-containing alginate solution was added dropwise to 500 ml of a stirred 0.1 molar aqueous calcium chloride solution at 5° C.

A ball-shaped product of immobilized enzyme on calcium alginate was obtained, which was further washed with boric acid/sodium borate/HCl buffer. The preparation exhibited an enzyme activity of 0.55 nkat/mg protein.

EXAMPLE 3

Oxidation of R,S-norreticuline to 1,2-dehydronorreticuline

To an aqueous solution of 100 mg (316 $\mu$Moles) R,S-norreticuline in 100 ml boric acid/sodium borate/HCl buffer solution (0.1 molar, pH=8.9) were added 10 ml of an enzyme preparation of S-tetrahydroprotoberberineoxidase (2.1 nkat/mg; 0.15 mg protein/ml). The reaction temperature was 37° C. Stirring was carried out with the admission of air for 16 hours. The progress of the reaction was controlled by taking out specimens and photometric analysis. After 16 hours, a 100% conversion of S-norreticuline into 1,2-dehydronorreticuline was observed. The R-norreticuline remained unchanged.

EXAMPLE 4

Oxidation of R,S-corypalmine to jatrorrhizine

To 100 ml aqueous solution of 5 mg (14.7 $\mu$Moles) R,S-corypalmine boric acid/sodium borate/HCl buffer (pH=8.9, 0.1 molar), 10 ml of an enzyme preparation of S-tetrahydroprotoberberineoxidase (2.1 nkat/mg and 0.15 mg protein/ml) were added. The reaction temperature was 37° C. Stirring was carried out with the admission of air for 2 hours. The progress of the reaction was controlled by taking out specimens and photometric analysis.

After 2 hours, a 100% conversion of S-corypalmine into jatrorrhizine was observed. The R-corypalmine remained unchanged.

EXAMPLE 5

Conversion of S-norreticuline to R-norreticuline (a) 50 g S-tetrahydroprotoberberineoxidase immobilized on calcium alginate (in the form of pearls), in a manner comparable to Example 2, having an enzyme activity of 0.2 nkat were shaken at a temperature of 30° C. for 150 hours with the admission of air in a solution of 30 mg S-norreticuline in 100 ml aqueous buffer solution (0.1 molar, pH=8.9) consisting of boric acid/sodium borate HCl. By photometric analysis, a complete conversion from S-norreticuline to 1,2-dehydronorreticuline was observed.

Subsequently, filtration was carried out and to the filtrate, 20 mg sodium boranate was added in portions. The originally yellow solution was immediately decolorized. A 1:1 mixture of S-norreticuline and R-reticuline was obtained.

(b) The S/R-norreticuline obtained according to (a) was brought to a pH=8.9 by addition of 0.1M hydrochloric acid and subjected to an enzymatic oxidation as described under (a).

After reduction, a mixture was obtained containing 3 parts of R-norreticuline and 1 part of S-norreticuline.

EXAMPLE 6

Oxidation of R,S-canadine to berberine

The method of Example 4 was repeated with the difference being that instead of R,S-corypalmaine, 5 g (14.7 mMole) R,S-canadine were used.

After 2 hours, a 100% conversion of S-canadine to berberine was observed. The R-canadine remained unchanged.

EXAMPLE 7

Oxidation of R,S[1-(3′,5′-dihydroxy-benzyl)-6methoxy-1,2,3,4-tetrahydroisoquinoline]

The method of Example 3 was repeated with the difference being that instead of R,S-norreticuline, 100 mg R,S-[1-(3′,5′-dihydroxy-benzyl)-6-methoxy-1,2,3,4-tetrahydroisoquinoline] were used.

After 16 hours, a 100% conversion of S-[1-(3′,5′-dihydroxy-benzyl)-6-methoxy-1,2,3,4-tetrahydroisoquinoline] to [1-(3′,5′-dihydroxy-benzyl)-6-methoxy-3,4-dihydroisoquinoline] was observed. The R-form remained unchanged.

While only several embodiments and examples of the present invention have been described, it is obvious that many changes and modifications may be made thereunto, without departing from the spirit and scope of the invention.

What is claimed is:
1. The compound s-tetrahydroproberberineoxidase having the following parameters:
   (a) molar weight: 100,000±10% as determined by gel filtration;
   (b) isoelectric point is 5.7;
   (c) catalytic activity occurs at 40° C.;
   (d) catalytic activity occurs at pH of 6-10;
   (e) $K_M$ value for R,S-corypalmine at 40° C. and pH 8.9 is 1.3 µMoles;
   (f) Intensity maximum of the fluorescense-emission spectrum is 520 nm at an excitation wavelength of 450 nm;
   (g) complete and reversible inhibition is exhibited in the presence of a member selected from the group consisting of acetylacetone and morin; and
   (h) prosthetic group flavin.
2. The composition of claim 1, wherein catalytic activity occurs at pH=8.9.
3. A method for producing S-tetrahydroproberberineoxidase having the following parameters:
   (a) molar weight: 100,000±10% as determined by gel filtration;
   (b) isoelectric point is 5.7;
   (c) catalytic activity occurs at 40° C.;
   (d) catalytic activity occurs at pH of 6-10;
   (e) $K_M$ value for R,S-corypalmine at 40° C. and pH 8.9 is 1.3 µMoles;
   (f) intensity maximum of the fluoroescense-emission spectrum is 520 nm at an excitation wavelength of 450 nm;
   (g) complete and reversible inhibition is exhibited in the presence of a member selected from the group consisting of acetylacetone and morin; and
   (h) prosthetic group flavin, comprising the step of extracting said S-tetrahydroprotoberberineoxidase from a plant material from a member of a family selected from the group consisting of Papaveraceae, Berberidaceae, Menispermaceae, Annonaceae, Ranunculaceae, and a combination thereof.
4. The method of claim 3, comprising the steps of:
   (a) destroying the structure of the cells other cell cultures of said plant material; and
   (b) dissolving the plant material from step (a) in an aqueous preparation of pH 6-10.
5. The method according to claim 4, wherein said aqueous preparation is a buffer solution.
6. The method of claim 4, further comprising the steps of:
   (c) adding an electrolyte to said aqueous preparation to precipitate proteins;
   (d) dissolving said precipitated proteins in an aqueous buffer solution; and
   (e) subjecting said precipitated proteins from step (d) to a gel filtration, resulting in the formation of an eluate, so that separation of unchanged materials occurs.
7. The method of claim 6, wherein step (c) occurs by addition of an ammonium sulfate electrolyte.
8. The method of claim 6, further comprising the step of separating said precipitated proteins, obtained in step (e), with ion-exchangers.
9. The method of claim 6, further comprising the step of cleaning said eluate obtained in step (e) with potassium chloride solutions of varying concentration.
10. A method for the enzymatic oxidation of a compound of the general formula:

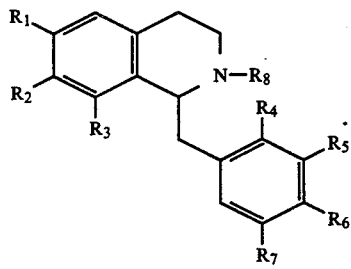

with S-configuration, wherein
$R_1$, $R_2$ $R_5$, $R_6$ and $R_7$ are independently elected from the group consisting of a hydrogen atom and hydroxy, alkyl and alkoxy groups;
$R_3$ is a member selected from the group consisting of hydrogen and an —OH group;
$R_4$ stands for hydrogen; and
$R_8$ stands for a member selected from the group consisting of hydrogen and an alkyl group with 1-3 carbon atoms; comprising the step of treating said compound with S-tetrahydroproberberineoxidase having the following parameters:
   (a) molar weight: 100,000±10% as determined by gel filtration;
   (b) isoelectric point is 5.7;

(c) catalytic activity occurs at 40° C.;
(d) cataltyic activity occurs at pH of 6–10;
(e) $K_M$ value for R,S-corypalmine at 40° C. and pH 8.9 is 1.3 μMoles;
(f) intensity maximum of the fluoroescense-emission spectrum is 520 nm at an excitation wavelength of 450 nm;
(g) completed and reversible inhibition is exhibited in the presence of a member selected from the group consisting of acetylacetone and morin; and
(h) prosthetic group flavin.

11. The method according to claim 10, wherein $R_4+R_8$ is a methylene bridge.

12. The method according to claim 10, wherein $R_1$, $R_2$, $R_5$ and $R_6$ are independently selected from the group consisting of —OH, methyl, ethyl, methoxy and ethoxy.

13. The method according to claim 10, wherein $R_1+R_2$ is a dioxaalkylene ring with 1 to 2 methylene groups.

14. The method according to claim 10, wherein $R_5+R_6$ is a dioxalkylene with 1 to 2 methylene groups.

15. The method of claim 10, wherein $R_8$ is a member selected from the group consisting of a hydrogen atom and a methyl group.

16. The method of claim 10, wherein said treating step comprises the steps of:
adding to an aqueous preparation of a member from the group consisting of S-tetrahydroprotoberberine and S-1-benzyl-1,2,3,4-tetrahydroisoquinoline, a preparation in which S-tetrahydroprotoberberineoxidase is present in an immobilized form; and
stirring said preparation in the presence of oxygen.

17. The method of claim 16, wherein said stirring step occurs in the presence of air.

18. The method of claim 16, further comprising the steps of:
(a) enzymatically oxidizing an enantiomer R,S-mixture of a member selected from the group consisting of tetrahydroprotoberberine and 1-benzyl-1,2,3,4-tetrahydroisoquinoline so that the R-form of said enantiomer mixture may be retained while enzymatically oxidizing, selectively, the S-form of said enantiomer mixture;
(b) reducing the products of said enzymatic oxidation obtained from step (a) with recovery of the R-form and the R,S-mixture;
(c) returning said R,S-mixture to step (a); and
(d) repeating steps (a)–(c) until a sufficient quantity of R-form is recovered.

19. An enzymatically acting composition comprising as an active substance an effective amount of S-tetrahydroprotoberberineoxidase having the following parameters:
(a) molar weight: 100,000±10% as determined by gel filtration;
(b) isoelectric point is 5.7;
(c) catalytic activity occurs at 40° C.;
(d) catalytic activity occurs at pH of 6–10;
(e) $K_M$ value for R,S-corypalmine at 40° C. and pH 8.9 is 1.3 μMoles;
(f) intensity maximum of the fluoroescense-emission spectrum is 520 nm at an excitation wavelength of 450 nm;
(g) complete and reversible inhibition is exhibited in the presence of a member selected from the group consisting of acetylacetone and morin; and
(h) prosthetic group flavin.

* * * * *